United States Patent
Sala et al.

(10) Patent No.: US 9,574,237 B2
(45) Date of Patent: Feb. 21, 2017

(54) METHOD FOR DIFFERENTIATING FERTILE AND STERILE PLANT LINES BY DETECTION OF POLYMORPHIC MARKERS IN CHLOROPLAST DNA

(71) Applicant: Anglo Netherlands Grain B.V., DR Rotterdam (NL)

(72) Inventors: Carlos Sala, Buenos Aires (AR); Maria Laura Ramos, Buenos Aires (AR); Mariano Bulos, Buenos Aires (AR); Emiliano Altieri, Buenos Aires (AR)

(73) Assignee: ANGLO NETHERLANDS GRAIN B.V., Rotterdam (NL)

( * ) Notice: Subject to any disclaimer, the term of this patent is extended or adjusted under 35 U.S.C. 154(b) by 805 days.

(21) Appl. No.: 13/686,198

(22) Filed: Nov. 27, 2012

(65) Prior Publication Data

US 2013/0167270 A1   Jun. 27, 2013

Related U.S. Application Data

(60) Provisional application No. 61/563,925, filed on Nov. 28, 2011.

(51) Int. Cl.
*C12Q 1/68* (2006.01)

(52) U.S. Cl.
CPC ............ *C12Q 1/6881* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| | | |
|---|---|---|
| EP | 1950290 | 7/2008 |
| EP | WO2009130307 | 10/2009 |
| FR | 2942583 | 9/2010 |
| IN | WO0122805 | 4/2001 |
| IN | WO0154487 | 8/2001 |
| JP | WO9509910 | 4/1995 |
| JP | WO2004005515 | 1/2004 |
| JP | WO2007049730 | 5/2007 |
| JP | WO2009098838 | 8/2009 |
| JP | WO2009113249 | 9/2009 |
| WO | WO9314624 | 8/1993 |
| WO | WO9619104 | 6/1996 |
| WO | WO9621010 | 7/1996 |
| WO | WO9709873 | 3/1997 |
| WO | WO02098209 | 12/2002 |

OTHER PUBLICATIONS

Cato et al. (Theor. Appl. Genet. (1996) 93: pp. 587-592).*
Kumashiro T et al: "A new source of cytoplasmic male sterile tobacco obtained by fusion between Nicotiana tabacum and X-irradiated N. africana protoplasts", Plant Science, Elsevier Ireland Ltd, IE, vol. 55, No. 3:247-254. Jan. 1, 1988.
Lorenz M., Weihe, A., Borner, T.: "DNA fragment of organellar origin in random amplified polymorphic DNA (RAPD) patterns of sugar beet (*Beta vulgaris* L.)", Theor. Appl. Genet., vol. 88:775-779. Jan. 1, 1994.
International Search Report for International Patent Application No. PCT/IB2012/002893(2013).
Written Opinion of the International Searching Authority for International Patent Application No. PCT/IB2012/002893 (2013).
Berville A., Faivre-Rampant P., Santoni S., Moreau E (1990) Controle de la purete des semences de base de prebase male-steriles cytoplasmiques par hybridation moleculaire avec un plasmide mitochondrial. Agronomie 10: 727-734.
Santoni A., Faivre-Rampant P., Moreau E., Berville A.. (1991) Rapid control of purity for the cytoplasm of male-sterile seed stocks by means of a dot hybridization assay. Molecular and Cellular Probes 5:1-9.
Triboush S.O., Danilenko N.G., DAvidenko O.G. (1998). A method for isolation of chloroplast DNA from sunflower. Plant Molecular Biology Reporter 16:183-189.
Timme R.E., Kuehl J.V., Boore J.L., Jansen R.K. (2007) a comparative análisis of the Lactuca and Helianthus (Asteraceae) plastid genomes: identification of divergent regions and categorization of shard repeats. American Journal of Botany 94:302-312.
Allen, J.O., Fauron, C.M., Minx, P., Roark, L., Oddiraju, S., Lin, G.N., Meyer, L., Sun, H., Kim, K., Wang, C., Du, F., Xu, D., Gibson, M., Cifrese, J., Clifton, S.W., Newton, K.J., 2007. Comparisons among two fertile and three male-sterile mitochondrial genomes of maize. Gentics 117, 1173-1192.
Balk, J. and Leaver, C.J. 2001. The PET1-CMS Mitochondrial Mutation in Sunflower is Associated with Premature Programmed Cell Death and Cytochrome c Release. The Plant Cell, vol. 13, 1803-1818.
Borsch, T. and Quandt, D. 2009 Mutational dynamics and phylogenetic utility of noncoding chloroplast DNA. Plant Systematics and Evolution 282:169-199.
Bryan GJ, McNicoll J, Ramsay G, Meyer RC, DeJong WS. 1999. Polymorphic simple sequence repeat markers in chloroplast genomes of Solanaceous plants. Theor Appl Genet;99: 859-67.
Chase, C.D., 2007. Cytoplasmic male sterility: a window to the world of plant mitochondrial-nuclear interactions. Trends Genet. 23, 81-90.
de la Canal, L.; D. Crouzillat, F. Quetier and G. Ledoigt. 2001. A transcriptional alteration on the atp9 gene is associated with a sunflower male-sterile cytoplasm. Theor Appl Genet 102:1185.
Demesure B, Sodzi N, Petit RJ. 1995. A set of universal primers for amplification of polymorphic non-coding regions of mitochondrial and chloroplast DNA in plants. Molecular Ecology. 4:129-131.

(Continued)

*Primary Examiner* — Brent Page
*Assistant Examiner* — Jared Shapiro
(74) *Attorney, Agent, or Firm* — Proskauer Rose LLP

(57) ABSTRACT

Disclosed are methods for differentiating fertile and sterile plant lines by detecting markers in chloroplast DNA from plants that have not yet flowered as well as from plant seeds. The method may be applied in selecting a seed lot based on the level of contamination of normal fertile plant line seeds being below a predetermined threshold, e.g., below 1% or 0.1%.

24 Claims, 13 Drawing Sheets

(56) References Cited

OTHER PUBLICATIONS

Dumolin-Lapegue S, Pemonge M-H, Petit RJ. 1997. An enlarged set of consensus primers for the study of organelle DNA in plants. Molecular Ecology. 6:393-398.
Gray M.W., Lang BF, Cedergren R., Golding G.B., Lemieux C., Sankoff D., Turmel M., Brossard N., Delage E., Littlejohn T.G., Plante I, Rioux P, Saint-Louis D, Zhu Y, Burger G. 1998. Genome structure and gene content in protist mitochondrial DNAs. Nucleic Acids Res.26:865-878.
Gutierres, S., Sabar, M., Lelandais, G., Chetrit, P., Diolez, P., Degand, H., Boutry, M., Vedel, F., de Kouchkovsky, Y., and DePaepe, R. 1997. Lack of mitochondrial and nuclear-encoded subunits of complex I and alteration of the respiratory chain in Nicotiana sylvestris mitochondrial deletion mutants. Proc. Natl. Acad. Sci. USA 94, 3436-3441.
Field D, Wills C.1996. Long, polymorphic microsatellite in simple organisms. Proceedings of Royal Society of London B Biological Sciences, 263, 209-215.
Forsberg, R.A and Smith R.R. 1980.Sources, maintainance, and utilization of parental material in Hybridization of crop plants (eds Fehr W.R and Hadley H.H.). ASA CASSA, WI, USA. pp. 65-81.
Hanson, M.R., Bentolila, S. 2004. Interaction of mitochondrial and nuclear genes that affect male gametophyte development. Plant Cell 16, 154-S169.
Horn, R., R. H. Kohler, and K. Zetsche. 1991. A mitochondrial 16 kDa protein is associated with cytoplasmic male sterility in sunflower. Plant Mol. Biol. 7, 29-36.
Kohler RH, Horn R, Lossl A, Zetsche K.1991. Cytoplasmic male sterility in sunflower is correlated with the co-transcription of a new open reading frame with the atpA gene. Mol Gen Genet 227:369-376.
Kubo, T., Mikami, T., 2007. Organization and variation of angiosperm mitochondrial genome. Physiol. Plant. 129, 6-13.
Kubo T, Newton KJ. 2008. Angiosperm mitochondrial genomes and mutations. Mitochondrion 8: 5-14.
Laver HK, Reynolds SJ, Moneger F, Leaver CJ. 1991. Mitochondrial genome organization and expression associated with cytoplasmic male sterility in sunflower (Helianthus annuus). Plant J 1:185-193.
Olmstead RG, Palmer JD. 1994. Chloroplast DNA systematics: A review of methods and data analysis. Amer J Bot. 81: 1205-1224.
Powell W, Morgante M, McDevitt R, Vendramin GG, Rafalski JA. 1995. Polymorphic simple sequence repeat regions in chloroplast genomes: applications to the population genetics of pines. Proc Natl Acad Sci USA;92:7759-63.
Powell, W., Morgante, M., Doyle, J.J., McNicol, J.W., Tingey, S.V., Rafalski, A.J. 1996. Genepool variation in genus Glycine subgenus Soja revealed by polymorphic nuclear and chloroplast microsatellites. Genetics, 144: 793-803.
Satoh, M., Kubo, T., Nishizawa, S., Estiati, A., Itchoda, N., Mikami, T.2004. The cytoplasmic male-sterile type and normal type mitochondrial genomes of sugar beet share the same complement of genes of known function but differ in the content of expressed ORFs. Mol. Genet. Genomics 272, 247-256.
Schnable, P., and Wise, R.P. 1998. The molecular basis of cytoplasmic male sterility and fertility restoration. Trends Plant Sci. 3,175-180.
Taberlet P, Gielly L, Pautou G, Bouvet J. 1991. Universal primers for amplification of three non-coding regions of chloroplast DNA. Plant Molecular Biology. 17:1105-1109.
Wang Z, Weber JL, Zhong G, Tanksley SD. 1994. Survey of plant short tandem DNA repeats. Theor. Appl. Genet. 88: 1-6.
Weising K, Gardner RA. 1999. A set of conserved PCR primers for the analysis of simple sequence repeat polymorphisms in chloroplast genomes of dicotyledonous angiosperms. Genome 42: 9-19.
Wise, Robert R. 2006. The Diversity of Plastid Form and Function. Advances in Photosynthesis and Respiration. 23: 3-26.
Wolfe, K.H., Li, W.H., and Sharp, P.M. 1987. Rates of nucleotide substitution vary greatly among plant mitochondrial, plastid, and nuclear DNAs, P. Natl Acad. Sci. USA. vol. 84, No. 24, pp. 9054-9058.

\* cited by examiner

| No. | Genotype | Sterile/Fertile | Type of Line or Hybrid |
|---|---|---|---|
| 1 | VA140 | Sterile | A line |
| 2 | VB141 | Fertile | B line |
| 3 | CMS GM40 | Sterile | A line |
| 4 | GM40 | Fertile | B line |
| 5 | CMS GM1606 | Sterile | A line |
| 6 | GM1606 | Fertile | B line |
| 7 | A837 | Sterile | A line |
| 8 | B838 | Fertile | B line |
| 9 | A749 | Sterile | A line |
| 10 | B750 | Fertile | B line |
| 11 | A769 | Sterile | A line |
| 12 | B770 | Fertile | B line |
| 13 | CMS HA89 | Sterile | A line |
| 14 | HA89 | Fertile | B line |
| 15 | R54 | Fertile (cms/$Rf1Rf1$) | R line |
| 16 | R81 | Fertile (cms/$Rf1Rf1$) | R line |
| 17 | R702 | Fertile (cms/$Rf1Rf1$) | R line |
| 18 | R2043 | Fertile (cms/$Rf1Rf1$) | R line |
| 19 | R720 | Fertile (cms/$Rf1Rf1$) | R line |
| 20 | RHA274 | Fertile (cms/$Rf1Rf1$) | R line |
| 21 | RHA271 | Fertile (cms/$Rf1Rf1$) | R line |
| 22 | HAR1 | Fertile | Unknown |
| 23 | HAR2 | Fertile | Unknown |
| 24 | HAR3 | Fertile | Unknown |
| 25 | HAR4 | Fertile | Unknown |
| 26 | HAR5 | Fertile | Unknown |
| 27 | P1000 | Fertile (Cms/$Rf1rf1$) | Commercial hybrid |
| 28 | P15 | Fertile (Cms/$Rf1rf1$) | Commercial hybrid |
| 29 | P102 CL | Fertile (Cms/$Rf1rf1$) | Commercial hybrid |
| 30 | Aromo 10 | Fertile (Cms/$Rf1rf1$) | Commercial hybrid |
| 31 | P68 CL | Fertile (Cms/$Rf1rf1$) | Commercial hybrid |
| 32 | P33 | Fertile (Cms/$Rf1rf1$) | Commercial hybrid |

FIG. 1: Sunflower genotypes used in this study.

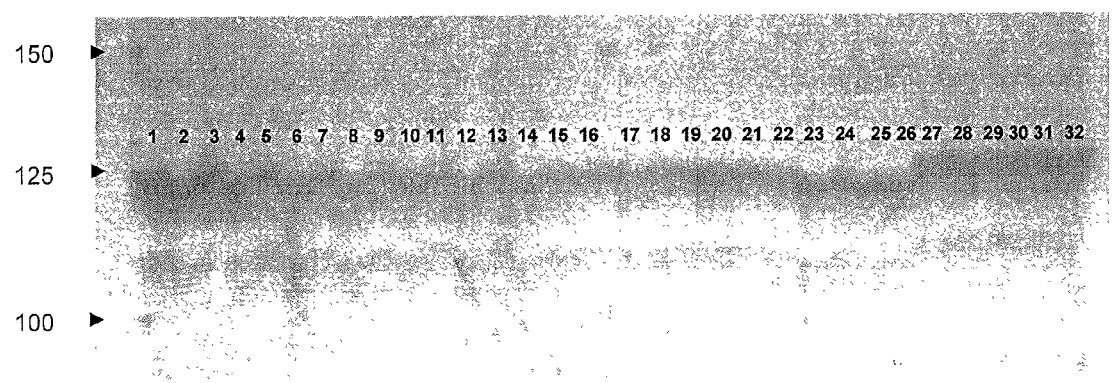
FIG. 2: Polymorphic cpSSR- 7 marker on chloroplastic DNA extracted from sunflower leaf tissue, 1- VA140; 2- VB141; 3- CMS GM40; 4- GM40; 5- CMS GM1606; 6- GM 1606; 7- A837; 8- B838; 9- A749; 10- B750; 11- A769; 12- B770; 13-CMS HA89; 14- HA89; 15- R54; 16- R81; 17- R702; 18- R2043; 19- R720; 20- RHA274; 21- RHA271; 22- HAR1; 23- HAR2; 24- HAR3; 25- HAR4; 26- HAR5; 27- P1000; 28- P15; 29- P102 CL; 30- Aromo 10; 31- P68 CL; 32- P33.

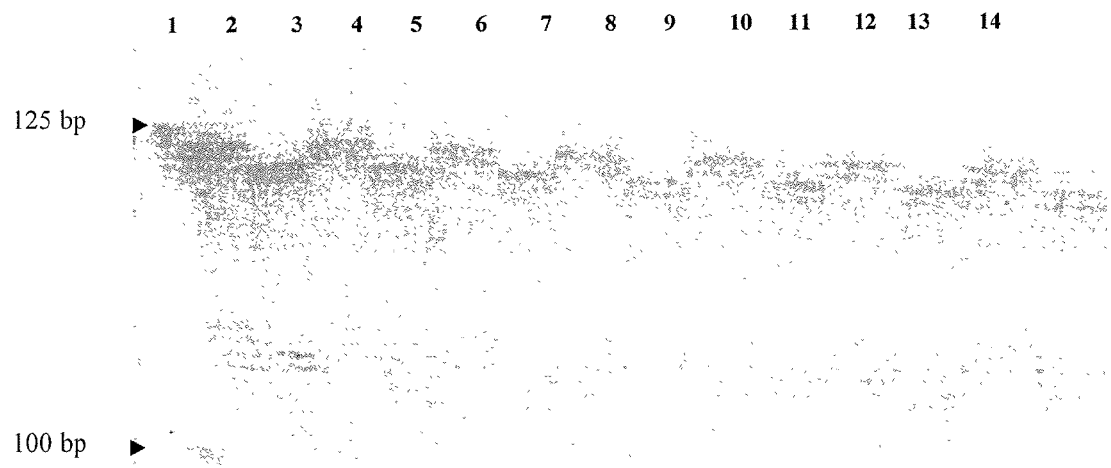
FIG. 3: Polymorphic cpSSR-7 marker on chloroplastic DNA extracted from proplastids of sunflower seeds, 1- VA140; 2- VB141; 3- CMS GM40; 4- GM40; 5- CMS GM1606; 6- GM 1606; 7- A837; 8- B838; 9- A749; 10- B750; 11- A769; 12- B770; 13-CMS HA89; 14- HA89.

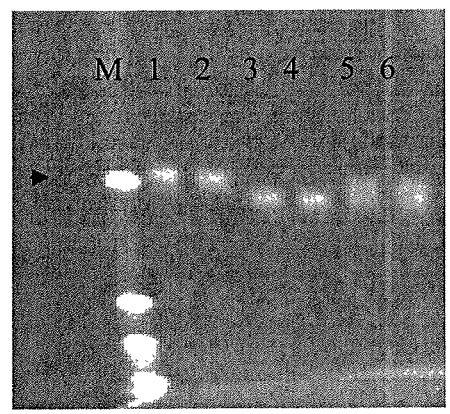
FIG. 4: Polymorphic cpSSR -7 marker on chloroplastic DNA extracted from proplastids of sunflower seeds analyzed in 4300 DNA Analyzer LiCor. M-molecular marker 700 Licor. 1 y 2- cms HA89; 3 y 4- HA89; 5 y 6- HA89:cms HA89 50:50.

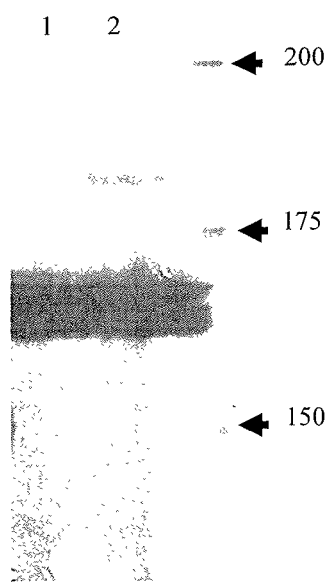
FIG. 5: Polymorphic cpSSR -2 marker on chloroplastic DNA extracted from proplastics of maize seeds. M-Molecular marker; 1-IT7EE42; 2-IT7EE42cms.

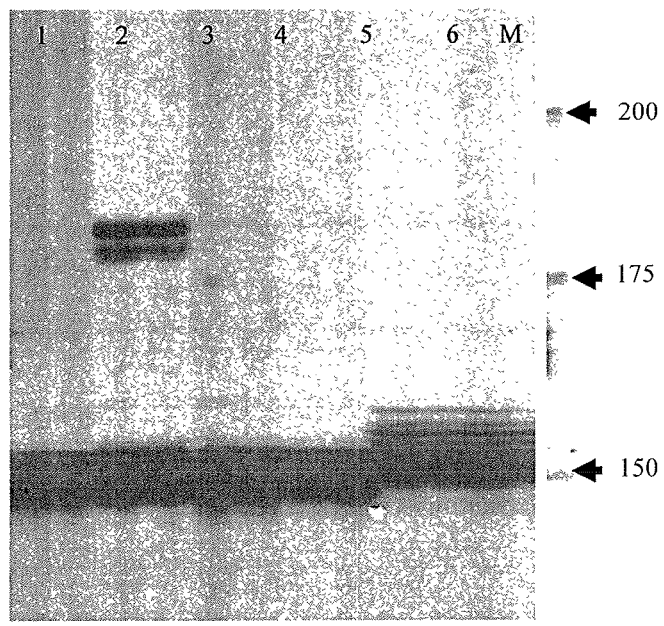
FIG. 6: Polymorphic cpSSR -2 marker on chloroplastic DNA extracted from wheat seeds. M- Molecular marker; 1-PR143; 2-PR189, 3-PR267, 4-PR270, 5-Bg9, 6-BTK242. 1, 2, 3 and 4 correspond to lines carrying the "*Thimopheevi*" cytoplasm.

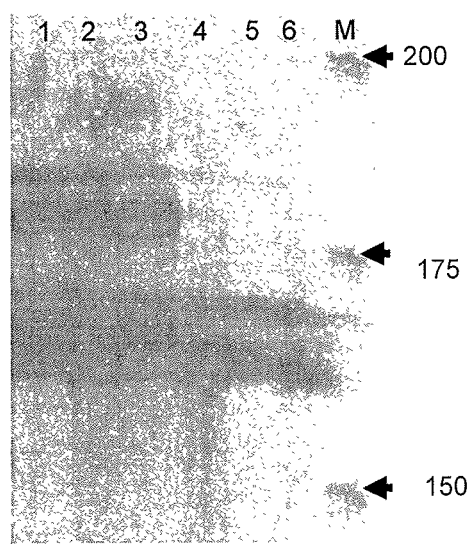
FIG. 7: Polymorphic cpSSR -2 marker on chloroplastic DNA extracted from sorghum seeds. M- Molecular marker; 1- R264W; 2- B375B; 3-B837BW; 4-S3N153; 5- S4N321RC; 6- A374F.

```
SEQ.ID3 : ACATCATTTTTTTTCTAAAAAAAGGAACTGCTTAATTCTACAAAAGAAAA : 465
SEQ.ID4 : ACATCATTTTTTTTCTAAAAAAAGGAACTGCTTAATTCTACAAAAGAAAA : 465
          ACATCATTTTTTTTCTAAAAAAAGGAACTGCTTAATTCTACAAAAGAAAA
                                                  506
SEQ.ID3 : AGTCTTTTTTTACGAGGTATAACTATAAATTCTTATGAAATCGACCATAG : 515
SEQ.ID4 : AGTCTTTTTTTACGAGGTATAACTATAAATTCTTATGAAAGCGACCATAG : 515
          AGTCTTTTTTTACGAGGTATAACTATAAATTCTTATGAAA CGACCATAG

SEQ.ID3 : ATCA : 519
SEQ.ID4 : ATCA : 519
          ATCA
```

FIG. 8: Partial nucleotide alignment of the complementary reverse sequences of the *rpoC1* intron from sterile (SEQ ID NO:3) and fertile lines (SEQ ID NO:4). The arrow points out the polymorphism which allows the discrimination between fertile and sterile lines.

```
                                                        506
                  ↓              ↓        ↓
SEQ.ID5  : AAGTCTTTTTTTACGAGGTATAACTATAAATTCTTATGAAAT-CGACCAT : 513
SEQ.ID3  : AAGTCTTTTTTTACGAGGTATAACTATAAATTCTTATGAAAT-CGACCAT : 513
SEQ.ID4  : AAGTCTTTTTTTACGAGGTATAACTATAAATTCTTATGAAAG-CGACCAT : 513
SEQ.ID6  : AAGTCTTTTTTTACGAGGTATAACTATAAATTCGTAGGAAAACCGACCTT : 514
SEQ.ID7  : AAGTCTTTTTTTACGAGGTATAACTATAAATTCTTATGAAAT-CGACCAT : 513
SEQ.ID8  : AAGTCTTTTTTTACGAGGTATAACTATAAATTCTTATGAAAT-CGACCAT : 513
SEQ.ID9  : AAGTCTTTTTTTACGAGGTATAACTATAAATTCTTATGAAAT-CGACCAT : 513
SEQ.ID10 : AAGTCTTTTTTTACGAGGTATAACTATAAATTCTTATGAAAT-CGACCAT : 513
SEQ.ID11 : AAGTCTTTTTTTACGAGGTATAACTATAAATTCTTATGAAAT CGACCAT : 513
SEQ.ID12 : AAGTCTTTTTTTACGAGGTATAACTATAAATTCTTATGAAAT-CGACCAT : 513
           AAGTCTTTTTTTACGAGGTATAACTATAAATTCtTAtGAAAt CGACCaT

SEQ.ID5  : AGATCA : 519
SEQ.ID3  : AGATCA : 519
SEQ.ID4  : AGATCA : 519
SEQ.ID6  : AGGTCT : 520
SEQ.ID7  : AGATCA : 519
SEQ.ID8  : AGATCA : 519
SEQ.ID9  : AGATCA : 519
SEQ.ID10 : AGATCA : 519
SEQ.ID11 : AGATCA : 519
SEQ.ID12 : AGATCA : 519
           AGaTCa
```

FIG. 9: Partial nucleotide alignment of the complementary reverse sequences of the intron *rpoC1* from lines RIG (SEQ ID NO:5), PET1 (SEQ ID NO:3), HA89 (SEQ ID. 4), PET2 (SEQ ID NO:6), ANN2 (SEQ ID NO:7), GIG1 (SEQ ID NO:8), ANN3 (SEQ ID NO:9), MAX1 (SEQ ID NO:10), PEF1 (SEQ ID NO:11), and ANN4 (SEQ ID NO:12) with different cytoplasms. The arrow is points out the polymorphism at the SNP G506T/A.

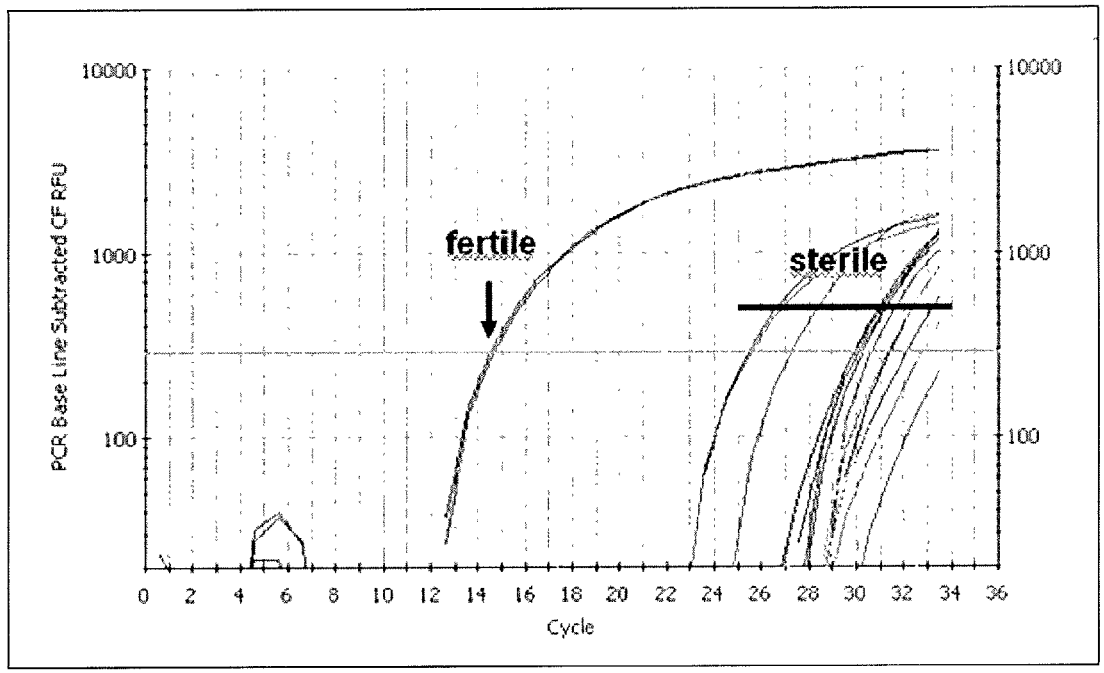

FIG. 10: SNP detection to differentiate fertile from sterile cytoplasms using Real Time PCR and SYBR Green I methodology. The plot displays the units of relative fluorescence (RFU) in function of numbers of amplification cycles of samples carrying the fertile and sterile cytoplams. Using the same amount of cpDNA input in the PCR reactions, the early Ct value (Ct number of amplification cycles threshold) indicates the specific detection of samples with fertile cytoplams.

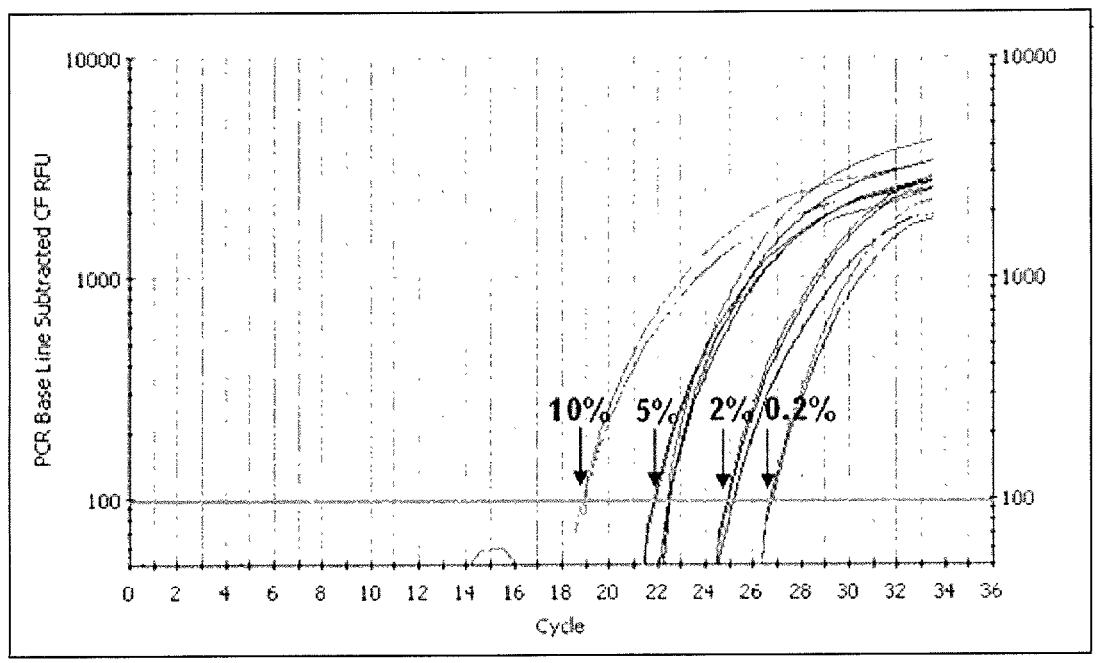
FIG. 11: SNP detection to differentiate fertile seeds contaminating sterile seed lots. The plot displays the units of relative fluorescence (RFU) in function of the number of amplification cycles. Differences in Ct (number of amplification cycles threshold) values indicate different levels of contamination by seeds with fertile cytoplasm in the samples.

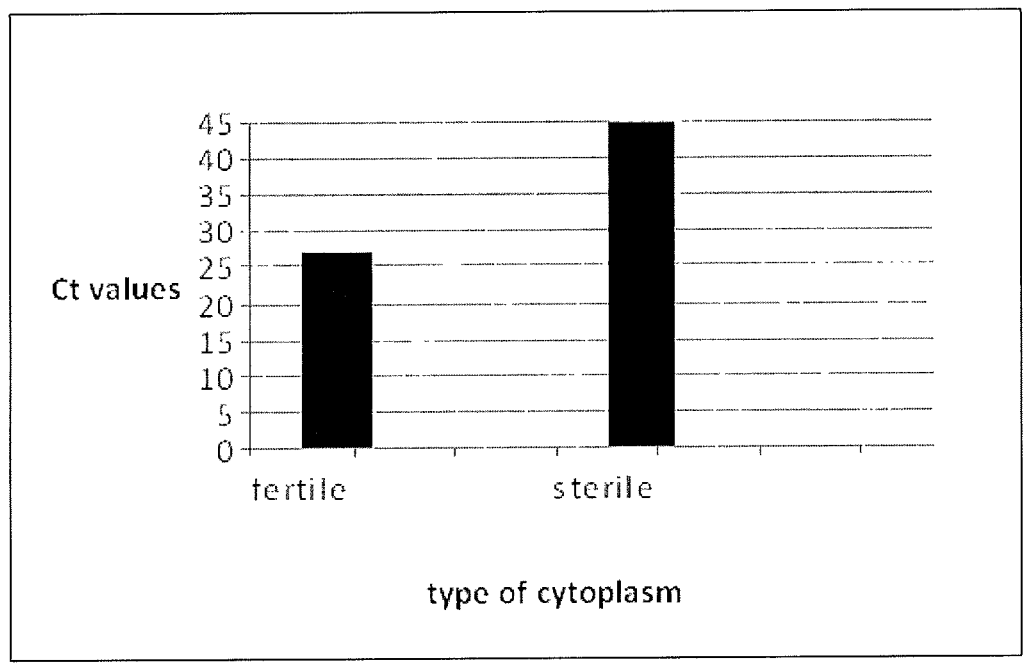
FIG. 12: TaqMan assay for detection of fertile or "normal" cytoplasm. The sample carrying the fertile cytoplasm shows the lowest Ct value, indicating the specific identification of the polymorphism by the probe. Meanwhile, the sterile cytoplasm sample shows the highest Ct value, indicating that the polymorphism present in this samples was not detected.

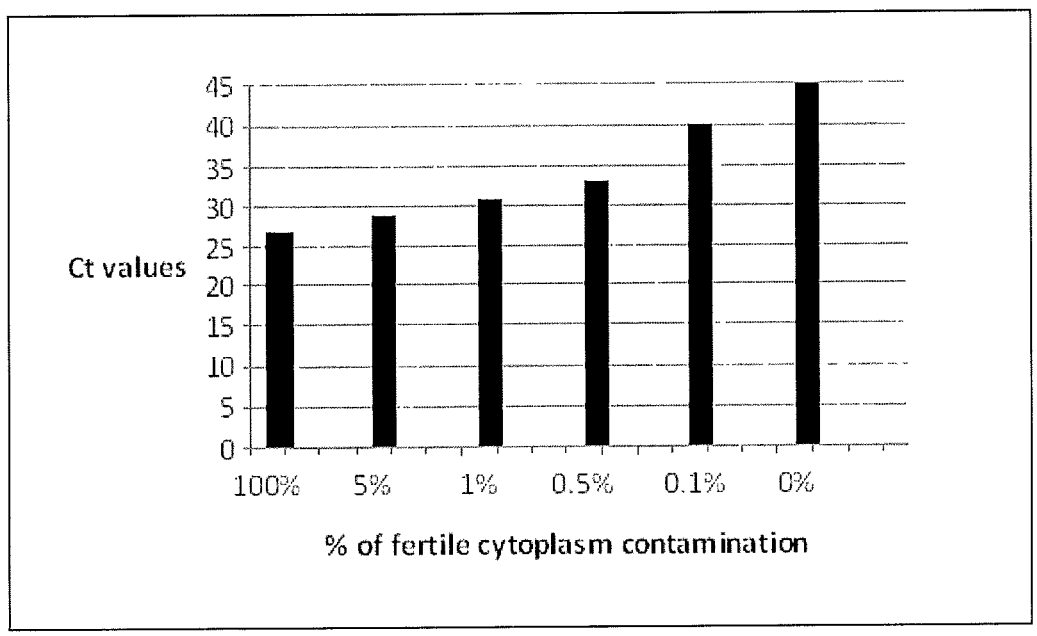
FIG. 13: TaqMan assay to determine fertile cytoplasm contamination levels. Ct values increase as a function of fertile cytoplasm contamination. The lower Ct value indicates the higher level of fertile cytoplasm contamination.

SEQUENCE LISTING

<160> NUMBER OF SEQ ID NOS: 16

<210> SEQ ID NO 1
<211> LENGTH: 24
<212> TYPE: DNA
<213> ORGANISM: Helianthus annuus L.

<400> SEQUENCE: 1
gaattaggga tgtattcaag acgc       24

<210> SEQ ID NO 2
<211> LENGTH: 24
<212> TYPE: DNA
<213> ORGANISM: Helianthus annuus L.

<400> SEQUENCE: 2
ggagttctcg ctttcagatt ctag       24

<210> SEQ ID NO 3
<211> LENGTH: 453
<212> TYPE: DNA
<213> ORGANISM: Helianthus petiolaris ssp petiolaris Nutt

<400> SEQUENCE: 3
tgatctatgg tcgatttcat aagaatttat agttatacct cgtaaaaaaa gactttttct    60
tttgtagaat taagcagttc ctttttttag aaaaaaaatg atgttcaagt aagcaaatag   120
aaaggatgtc atggttacaa gagtctatct atcgcatata gactttaatc gtggcctaac   180
cgtcgaggtg aagtcgggac ctaaaagatc gaatggaaca gtacatagac aagtaaattc   240
cttatgaatt ccaaggtact ctctttaatt aagaattacg gattcatcat tcgagaggaa   300
gtagactact caagaatttc acatttcatt tatgtcataa ttgaataaag aattcataaa   360
atctaaataa aaataataag gaagacagaa tcaatgaagt tttgcttgat tttcactgaa   420
aacttgagta aggagtagat cctttggag ttt                                 453

<210> SEQ ID NO 4
<211> LENGTH: 451
<212> TYPE: DNA
<213> ORGANISM: Helianthus annuus L.

<400> SEQUENCE: 4

```
tgatctatgg tcgctttcat aagaatttat agttatacct cgtaaaaaaa gacttttcct      60
tttgtagaat taagcagttc cttttttag aaaaaaaatg atgttcaagt aagcaaatag      120
aaaggatgtc atggttacaa gagtctatcc gcatatagac tttaatcgtg gcctaaccgt     180
cgaggtgaag tcgggaccta aaagatcgaa tggaacagta catagacaag taaattcctt     240
atgaattcca aggtactctc tttaattaag aattacggga ttcatcattc gagaggaagt     300
agactactca agaatttcac atttcattta tgtcataatt gaataaagaa ttcataaaat     360
ctaaataaaa ataataagga agacagaatc aatgaagttt tgcttgattt tcactgaaaa     420
cttgagtaag gagtagatcc ttttggagtt t                                    451
```

<210> SEQ ID NO 5
<211> LENGTH: 454
<212> TYPE: DNA
<213> ORGANISM: Helianthus rigidus (Cass.) Desf. (=Helianthus
       pauciflorus Nutt.)

<400> SEQUENCE: 5

```
tgatctatgg tcgatttcat aagaatttat agttatacct cgtaaaaaaa gacttttcct      60
tttgtagaat taagcagttc cttttttag aaaaaaaatg atgttcaagt aagcaaatag      120
aaaggatgtc atggttacaa gagtctatct atcgcatata gactttaatc gtggcctaac     180
cgtcgaggtg aagtcgggac ctaaaagatc gaatggaaca gtacatagac aagtaaattc     240
cttatgaatt ccaaggtact ctctttaatt aagaattacg ggattcatca ttcgagagga     300
agtagactac tcaagaattt cacatttcat ttatgtcata attgaataaa gaattcataa     360
aatctaaata aaaataataa ggaagacaga atcaatgaag ttttgcttga ttttcactga     420
aaacttgagt aaggagtaga tccttttgga gttt                                 454
```

<210> SEQ ID NO 6
<211> LENGTH: 455
<212> TYPE: DNA
<213> ORGANISM: Helianthus petiolaris ssp. petiolaris Nutt

<400> SEQUENCE: 6

```
agacctaagg tcggttttcc tacgaattta tagttatacc tcgtaaaaaa agactttttt      60
ttttggtaga attaagcagt tccttttttg gaaaaaaaaa tgatgttcaa gtaagcaaat     120
agaaaggatg tcatggttac aagagtctat ctatcgcata tagactttaa tcgtggccta     180
accgtcgagg tgaagtcggg acctaaaaga tcgaatggaa cagtacatag acaagtaaat     240
tccttatgaa ttccaaggta ctctctttaa ttaagaatta cgggattcat cattcgagag     300
gaagtagact actcaagaat ttcacatttc atttatgtca taattgaata agaattcat     360
aaaatctaaa taaaataat aaggaagcag aatcaatgaa attttgcttg attttcactg     420
aaaacttgag taaggagtag atccttttgg agttt                                455
```

<210> SEQ ID NO 7
<211> LENGTH: 455
<212> TYPE: DNA
<213> ORGANISM: Helianthus annuus L.

<400> SEQUENCE: 7

```
tgatctatgg tcgatttcat aagaatttat agttataccg cgtaaaaaaa gacttttct    60 tttgtagaat taagcagttc ctttttttag aaaaaaaaat gatgttcaag taagcaaata   120
gaaaggatgt catggttaca agagtctatc tatcgcatat agactttaat cgtggcctaa   180
ccgtcgaggt gaagtcggga cctaaaagat cgaatggaac agtacataga caagtaaatt   240
ccttatgaat tccaaggtac tctctttaat taagaattac gggattcatc attcgagagg   300
aagtagacta ctcaagaatt tcacatttca tttatgtcat aattgaataa agaattcata   360
aaatctaaat aaaataata aggaagacag aatcaatgaa attttgcttg attttcactg   420
aaaacttgag taaggagtag atccttttgg agttt                              455

<210> SEQ ID NO 8
<211> LENGTH: 455
<212> TYPE: DNA
<213> ORGANISM: Helianthus giganteus L

<400> SEQUENCE: 8
tgatctatgg tcgatttcat aagaatttat agttataccg cgtaaaaaaa gacttttct    60 tttgtagaat taagcagttc ctttttttag aaaaaaaaat gatgttcaag taagcaaata   120
gaaaggatgt catggttaca agagtctatc tatcgcatat agactttaat cgtggcctaa   180
ccgtcgaggt gaagtcggga cctaaaagat cgaatggaac agtacataga caagtaaatt   240
ccttatgaat tccaaggtac tctctttaat taagaattac gggattcatc attcgagagg   300
aagtagacta ctcaagaatt tcacatttca tttatgtcat aattgaataa agaattcata   360
aaatctaaat aaaataata aggaagacag aatcaatgaa attttgcttg attttcactg   420
aaaacttgag taaggagtag atccttttgg agttt                              455

<210> SEQ ID NO 9
<211> LENGTH: 346
<212> TYPE: DNA
<213> ORGANISM: Helianthus annuus L.

<400> SEQUENCE: 9
tgatctatgg tcgatttcat aagaatttat agttataccg cgtaaaaaaa gacttttct    60 tttgtagaat taagcagttc ctttttttag aaaaaaaaat gatgttcaag taagcaaata   120
gaaaggatgt catggttaca agagtctatt atcgcatata gactttaatc gtggcctaac   180
cgtcgaggtg aagtcgggac ctaaaagatc gaatggaaca gtacatagac aagtaaattc   240
cttatgaatt ccaaggtact ctctttaatt aagaattacg ggattcatca ttcgagagga   300
agtagactac tcaagaattt cacatttcat ttatgtcata attgaa                  346

<210> SEQ ID NO 10
<211> LENGTH: 454
<212> TYPE: DNA
<213> ORGANISM: Helianthus maximiliani Schrad

<400> SEQUENCE: 10
tgatctatgg tcgatttcat aagaatttat agttataccg cgtaaaaaaa gacttttct    60 tttgtagaat taagcagttc ctttttttag aaaaaaaatg atgttcaagt aagcaaatag   120
aaaggatgtc atggttacaa gagtctatct atcgcatata gactttaatc gtggcctaac   180
cgtcgaggtg aagtcgggac ctaaaagatc gaatggaaca gtacatagac aagtaaattc   240
cttatgaatt ccaaggtact ctctttaatt aagaattacg ggattcatca ttcgagagga   300
agtagactac tcaagaattt cacatttcat ttatgtcata attgaataaa gaattcataa   360
```
aatctaaata aaaataataa ggaagacaga atcaatgaag ttttgcttga ttttcactga    420
aaacttgagt aaggagtaga tcctttttgga gttt    454

```
<210> SEQ ID NO 11
<211> LENGTH: 454
<212> TYPE: DNA
<213> ORGANISM: Helianthus petiolaris ssp. fallax Heiser

<400> SEQUENCE: 11
```
tgatctatgg tcgatttcat aagaatttat agttatacct cgtaaaaaaa gactttttct    60
tttgtagaat taagcagttc ctttttttag aaaaaaaatg atgttcaagt aagcaaatag    120
aaaggatgtc atggttacaa gagtctatct atcgcatata gactttaatc gtggcctaac    180
cgtcgaggtg aagtcgggac ctaaaagatc gaatggaaca gtacatagac aagtaaattc    240
cttatgaatt ccaaggtact ctctttaatt aagaattacg ggattcatca ttcgagagga    300
agtagactac tcaagaattt cacatttcat ttatgtcata attgaataaa gaattcataa    360
aatctaaata aaaataataa ggaagacaga atcaatgaag ttttgcttga ttttcactga    420
aaacttgagt aaggagtaga tcctttttgga gttt    454

```
<210> SEQ ID NO 12
<211> LENGTH: 454
<212> TYPE: DNA
<213> ORGANISM: Helianthus annuus L.

<400> SEQUENCE: 12
```
tgatctatgg tcgatttcat aagaatttat agttatacct cgtaaaaaaa gactttttct    60
tttgtagaat taagcagttc ctttttttag aaaaaaaatg atgttcaagt aagcaaatag    120
aaaggatgtc atggttacaa gagtctatct atcgcatata gactttaatc gtggcctaac    180
cgtcgaggtg aagtcgggac ctaaaagatc gaatggaaca gtacatagac aagtaaattc    240
cttatgaatt ccaaggtact ctctttaatt aagaattacg ggattcatca ttcgagagga    300
agtagactac tcaagaattt cacatttcat ttatgtcata attgaataaa gaattcataa    360
aatctaaata aaaataataa ggaagacaga atcaatgaag ttttgcttga ttttcactga    420
aaacttgagt aaggagtaga tcctttttgga gttt    454

```
<210> SEQ ID NO 13
<211> LENGTH: 30
<212> TYPE: DNA
<213> ORGANISM: Helianthus annuus L.

<400> SEQUENCE: 13
```
acgaggtata actataaatt cttatgaaag    30

```
<210> SEQ ID NO 14
<211> LENGTH: 37
<212> TYPE: DNA
<213> ORGANISM: Helianthus annuus L.

<400> SEQUENCE: 14
```
ctacaaaaga aaaagtcttt ttttacgagg tataact    37

```
<210> SEQ ID NO 15
<211> LENGTH: 23
<212> TYPE: DNA
<213> ORGANISM: Helianthus annuus L.

<400> SEQUENCE: 15
```

```
tgtattcaag acgctcccca aaa                                          23
```

```
<210> SEQ ID NO 16
<211> LENGTH: 18
<212> TYPE: DNA
<213> ORGANISM: Helianthus annuus L.

<400> SEQUENCE: 16
atctatggtc gctttcat                                                18
```

METHOD FOR DIFFERENTIATING FERTILE AND STERILE PLANT LINES BY DETECTION OF POLYMORPHIC MARKERS IN CHLOROPLAST DNA

INCORPORATION BY REFERENCE OF SEQUENCE LISTING

This application contains references to amino acids and/or nucleic acid sequences that have been filed as sequence listing text file 13686198_sequence_listing.txt, file size of 8.7 KB, created on Mar. 21, 2016. The aforementioned sequence listing is hereby incorporated by reference in its entirety pursuant to 37 C.F.R. §1.52(e)(5).

BACKGROUND

This technology is directed to a method for differentiating fertile and sterile plant lines at the DNA level, by detecting polymorphisms in chloroplast DNA.

Hybrid vigor in crop plants has been recognized as a widespread and powerful tool to increase yields. Commercial hybrids are used extensively in many crops, including corn, sorghum, sugarbeet, colza, wheat, and sunflower.

Commercial hybrids have the greatest potential for crops when the hybrid seed can be produced reliably and economically. The three biological requirements for successful hybrid seed production are: (a) the presence of hybrid vigor; (b) elimination of fertile pollen in the inbred line that will act as female parent; and (c) adequate pollination by the inbred line that will act as male parent. If these biological requirements are met for a particular species, a practical program of seed production on a large scale may be developed to produce hybrids for use by farmers.

The second of the aforementioned requirements—the elimination of fertile pollen in a line that will act as female parent of the hybrid—has led scientists to endeavor to understand the biological mechanisms of obtaining male sterility in a hermaphrodite species. Accordingly, several procedures or systems were developed to obtain male sterility, including genetic male sterility, cytoplasmic male sterility, and nuclear-cytoplasmic male sterility. Nuclear-cytoplasmic male sterility, in particular, is widely used for commercial seed production of hybrid seed in hermaphrodite crop species (Wright, 1980).

Three types of inbred lines must be developed and maintained when employing a cytoplasmic-genetic system to produce hybrids, as in the case of hybrid corn, sorghum, pearl millet, sunflower, and other species. In this system, the female parent harbors factors in the cytoplasm of cells, which render it male-sterile in the absence of appropriate restorer genes in the nucleus. The cytoplasm of the female gamete, but not that of the male, is transmitted to the offspring, thereby making it possible to produce female populations which are free of any male-fertile individuals (Forsberg & Smith, 1980).

The female parent in the cytoplasmic genetic system must have two different, but phenotypically identical forms. One form is male sterile, with sterile cytoplasm (S) and with nonrestoring genes (rfrf) in the nucleus. The other form is male fertile, with normal, fertile, cytoplasm (N) and also with nonrestorer genes in the nucleus (rfrf). The male sterile version is referred to as the cytoplasmic male sterile (cms) line, the A line, or the sterile line. The normal male fertile version is called the maintainer line or the B line. Generally, the cms line is developed by crossing a normal male fertile line, as male, to a male sterile female with sterile cytoplasm and nonrestoring genes, followed by repeated backcrossing to the normal male fertile line. After the cms line has been developed, a cms line seed is produced for line maintenance by crossing the sterile cms line (S, rfrf) with the normal male fertile line (N, rfrf). All offspring from the cross will be male-sterile. The normal male fertile lines (or maintainer lines or B lines) are maintained by a routine selfing, sibbing, or open pollination in isolation.

The third type of inbred line in the cytoplasmic-genetic system is the restorer male parent. Accordingly, it must have the homozygous dominant genotype for fertility restoration (RfRf). These restorer lines, or R lines, can be developed by using a line with restorer genes as the donor parent and the genotype (line) desired for use as a restorer line as the recurrent parent in a series of backcrosses. It is very convenient if a donor parent also has sterile cytoplasm (S, RfRf) and is used as the female, because the presence of the restorer allele in segregating populations after each backcross is phenotypically apparent. The restorer male parent lines are fertile and are maintained by routine selfing, sibbing or open pollination in isolation.

For hybrid seed production, rows of the cms line are interplanted with rows of the fertility restorer line in ratios from 2:1 to 6:1. Hybrid seeds from the cross cms×restorer, are then harvested on the cms line.

SUMMARY OF THE TECHNOLOGY

One aspect of the technology is a method for differentiating normal fertile and sterile counterparts of an inbred line of a plant crop having a cytoplasmic or nuclear-cytoplasmic system of male sterility comprising the steps of: (a) extracting chloroplastic DNA; and (b) amplifying the chloroplastic DNA with one or more DNA markers, wherein said markers target DNA polymorphic differences between a normal fertile plant and a cytoplasmic male sterile plant line. In a related aspect, the chloroplastic DNA is extracted from seeds. In aspect, the DNA marker is an amplified fragment length polymorphism (AFLP), anchored microsatellite primed PCR (AMP-PCR), arbitrarily primed PCR (AP-PCR), allele-specific amplification (ASA), anchored simple sequence repeat (ASSR), cleaved amplified polymorphic sequence (CAPS), DNA amplification fingerprint (DAF), direct amplification of length polymorphism (DALP), direct amplification of microsatellite DNA by PCR (DAMD-PCR), DNA fragment length polymorphism (DFLP), digested RAMP (dRAMP), intron-retrotransposon amplified polymorphism (IFLP), inter-microsatellite PCR (IM-PCR), inter-retrotransposon amplified polymorphism (IRAP), inter-SSR amplification (ISA), inter-simple sequence repeats (ISSR), multiple arbitrary amplicon profiling (MAAP), microsatellite-primed PCR (MP-PCR), oligonucleotide ligation assay (OLA), randomly amplified hydbridizing microsatellites (RAHM), randomly amplified microsatellite polymorphism (RAMPO), randomly amplified microsatellites polymorphism (RAMP), randomly amplified microsatellites (RAMS), random amplified polymorphic DNA (RAPD), retrotransposon-based insertion polymorphism (RBIP), retrotransposon-microsatellite amplified polymorphism (REMAP), restriction fragment length polymorphism RFLP), selective amplification of microsatellite polymorphic loci (SAMPLE), sequence characterized amplified regions (SCAR), single nucleotide polymorphism (SNP), single primer amplification polymorphism (SPAR), sequence related amplified polymorphism (SRAP), sequence-specific amplification polymorphism (S-SAP), single strand conformation polymorphism (SSCP), simple sequence length polymorphism (SSLP), sequence tagged microsatellite region (STAR), sequence-tagged microsatellite site (STMS), short tandem repeat (STR), sequence-tagged-site (STS), Target Region Amplification Polymorphism (TRAP), variable number of tandem repeats (VNTR), or a simple sequence repeat (SSR). In one aspect of the technology, the DNA marker is cpSSR-2 or cpSSR-7. In another aspect of the technology, the DNA marker is a SNP in the intron of the gene sequence of rpoC1 that permits differentiation of the fertile and sterile cytoplasms of sunflower. In a related aspect, the DNA marker is a SNP in the intron of the gene sequence of rpoC1 that permits differentiation of the fertile and sterile cytoplasms of sunflower, whose sequences are set forth in SEQ ID NOs:3-12. In another aspect, the plant is alfalfa (*Medicago sativa*), onion (*Allium cepa*), maize (*Zea mays*), wheat (*Triticum aestivum*), rice (*Oryza sativa*), sunflower (*Helianthus annuus*), sorghum (*Sorghum bicolor*), carrot (*Daucus carota*), petunia (*Petunia hybrida*), canola (*Brassica napus*), sugarbeet (*Beta vulgaris*), or tobacco (*Nicotiana tabacum*). In yet another aspect of the technology, a seed lot is selected based on a level of contamination of normal fertile plant line seeds being below a predetermined threshold. In related aspects, the predetermined threshold is either 1% or less or 0.1% or less.

Yet another aspect of the technology is a method for detecting plant seed contamination of normal fertile plant seeds among cytoplasmic male sterile plant seeds, of an inbred line of plant crop having a cytoplasmic or nuclear-cytoplasmic system of male sterility, comprising the steps of: (a) extracting chloroplastic DNA from a bulk of seeds; and (b) amplifying the chloroplastic DNA with one or more DNA markers, wherein said markers target DNA polymorphic differences between a normal fertile plant and a cytoplasmic male sterile plant line. In a related aspect, the DNA marker is an amplified fragment length polymorphism (AFLP), anchored microsatellite primed PCR (AMP-PCR), arbitrarily primed PCR (AP-PCR), allele-specific amplification (ASA), anchored simple sequence repeat (ASSR), cleaved amplified polymorphic sequence (CAPS), DNA amplification fingerprint (DAF), direct amplification of length polymorphism (DALP), direct amplification of microsatellite DNA by PCR (DAMD-PCR), DNA fragment length polymorphism (DFLP), digested RAMP (dRAMP), intron-retrotransposon amplified polymorphism (IFLP), inter-microsatellite PCR (IM-PCR), inter-retrotransposon amplified polymorphism (IRAP), inter-SSR amplification (ISA), inter-simple sequence repeats (ISSR), multiple arbitrary amplicon profiling (MAAP), microsatellite-primed PCR (MP-PCR), oligonucleotide ligation assay (OLA), randomly amplified hydbridizing microsatellites (RAHM), randomly amplified microsatellite polymorphism (RAMPO), randomly amplified microsatellites polymorphism (RAMP), randomly amplified microsatellites (RAMS), random amplified polymorphic DNA (RAPD), retrotransposon-based insertion polymorphism (RBIP), retrotransposon-microsatellite amplified polymorphism (REMAP), restriction fragment length polymorphism RFLP), selective amplification of microsatellite polymorphic loci (SAMPLE), sequence characterized amplified regions (SCAR), single nucleotide polymorphism (SNP), single primer amplification polymorphism (SPAR), sequence related amplified polymorphism (SRAP), sequence-specific amplification polymorphism (S-SAP), single strand conformation polymorphism (SSCP), simple sequence length polymorphism (SSLP), sequence tagged microsatellite region (STAR), sequence-tagged microsatellite site (STMS), short tandem repeat (STR), sequence-tagged-site (STS), Target Region Amplification Polymorphism (TRAP), variable number of tandem repeats (VNTR), or a simple sequence repeat (SSR). In another aspect, the DNA marker is amplified and detected using Real Time PCR methodology. In a related aspect, the DNA marker is amplified using primers set forth in SEQ ID NOs:1 and 13. In a related aspect, the DNA marker is amplified and detected using Real Time PCR methodology coupled with a TAQMAN assay. In a related aspect, the DNA marker is amplified using the primers set forth in SEQ ID NOs:14 and 15 and the amplicon is probed with a fluorophore-labeled probe with a sequence set forth in SEQ ID NO:16. In yet another related aspect, the DNA marker is cpSSR-2 or cpSSR-7. In one aspect of the technology, the DNA marker is cpSSR-2 or cpSSR-7. In another aspect of the technology, the DNA marker is a SNP in the intron of the gene sequence of rpoC1 that permits differentiation of the fertile and sterile cytoplasms of sunflower. In another aspect, the plant is alfalfa (*Medicago sativa*), onion (*Allium cepa*), maize (*Zea mays*), wheat (*Triticum aestivum*), rice (*Oryza sativa*), sunflower (*Helianthus annuus*), sorghum (*Sorghum bicolor*), carrot (*Daucus carota*), petunia (*Petunia hybrida*), canola (*Brassica napus*), sugarbeet (*Beta vulgaris*), or tobacco (*Nicotiana tabacum*). In another aspect of the technology, a seed lot is selected based on a level of contamination of normal fertile plant line seeds being below a predetermined threshold. In related aspects, the predetermined threshold is either 1% or less or 0.1% or less.

Another aspect of the technology is a method of mitigating plant seed contamination of normal fertile plant seeds among cytoplasmic male sterile plant seeds, of an inbred line of plant crop having a cytoplasmic or nuclear-cytoplasmic system of male sterility, comprising: (a) extracting chloroplastic DNA from a bulk of seeds; (b) amplifying the chloroplastic DNA with one or more DNA markers, wherein said markers target DNA polymorphic differences between a normal fertile plant and a cytoplasmic male sterile plant line; and (c) selecting the seed if it is essentially free of contamination from a normal fertile plant line or rejecting the seed if it exhibits contamination from a normal fertile plant line. In a related aspect, the DNA marker is an amplified fragment length polymorphism (AFLP), anchored microsatellite primed PCR (AMP-PCR), arbitrarily primed PCR (AP-PCR), allele-specific amplification (ASA), anchored simple sequence repeat (ASSR), cleaved amplified polymorphic sequence (CAPS), DNA amplification fingerprint (DAF), direct amplification of length polymorphism (DALP), direct amplification of microsatellite DNA by PCR (DAMD-PCR), DNA fragment length polymorphism (DFLP), digested RAMP (dRAMP), intron-retrotransposon amplified polymorphism (IFLP), inter-microsatellite PCR (IM-PCR), inter-retrotransposon amplified polymorphism (IRAP), inter-SSR amplification (ISA), inter-simple sequence repeats (ISSR), multiple arbitrary amplicon profiling (MAAP), microsatellite-primed PCR (MP-PCR), oligonucleotide ligation assay (OLA), randomly amplified hydbridizing microsatellites (RAHM), randomly amplified microsatellite polymorphism (RAMPO), randomly amplified microsatellites polymorphism (RAMP), randomly amplified microsatellites (RAMS), random amplified polymorphic DNA (RAPD), retrotransposon-based insertion polymorphism (RBIP), retrotransposon-microsatellite amplified polymorphism (REMAP), restriction fragment length polymorphism RFLP), selective amplification of microsatellite polymorphic loci (SAMPLE), sequence characterized amplified regions (SCAR), single nucleotide polymorphism (SNP), single primer amplification polymorphism (SPAR), sequence related amplified polymorphism (SRAP), sequence-specific amplification polymorphism (S-SAP), single strand conformation polymorphism (SSCP), simple sequence length polymorphism (SSLP), sequence tagged microsatellite region (STAR), sequence-tagged microsatellite site (STMS), short tandem repeat (STR), sequence-tagged-site (STS), Target Region Amplification Polymorphism (TRAP), variable number of tandem repeats (VNTR), or a simple sequence repeat (SSR). In a related aspect, the DNA marker is cpSSR-2 or cpSSR-7. In one aspect of the technology, the DNA marker is cpSSR-2 or cpSSR-7. In another aspect of the technology, the DNA marker is a SNP in the intron of the gene sequence of rpoC1 that permits differentiation of the fertile and sterile cytoplasms of sunflower. In another aspect of the technology, plant is alfalfa (*Medicago sativa*), onion (*Allium cepa*), maize (*Zea mays*), wheat (*Triticum aestivum*), rice (*Oryza sativa*), sunflower (*Helianthus annuus*), sorghum (*Sorghum bicolor*), carrot (*Daucus carota*), petunia (*Petunia hybrida*), canola (*Brassica napus*), sugarbeet (*Beta vulgaris*), or tobacco (*Nicotiana tabacum*).

Another aspect of the technology is a plant seed lot produced by the process of: (a) extracting chloroplastic DNA from a bulk of seeds; (b) amplifying the chloroplastic DNA with one or more DNA markers, wherein said markers target DNA polymorphic differences between a normal fertile plant and a cytoplasmic male sterile plant line; and (c) selecting the seed lot if the level of contamination from normal fertile seeds is below a predetermined threshold. In another aspect, the DNA marker is an amplified fragment length polymorphism (AFLP), anchored microsatellite primed PCR (AMP-PCR), arbitrarily primed PCR (AP-PCR), allele-specific amplification (ASA), anchored simple sequence repeat (ASSR), cleaved amplified polymorphic sequence (CAPS), DNA amplification fingerprint (DAF), direct amplification of length polymorphism (DALP), direct amplification of microsatellite DNA by PCR (DAMD-PCR), DNA fragment length polymorphism (DFLP), digested RAMP (dRAMP), intron-retrotransposon amplified polymorphism (IFLP), inter-microsatellite PCR (IM-PCR), inter-retrotransposon amplified polymorphism (IRAP), inter-SSR amplification (ISA), inter-simple sequence repeats (ISSR), multiple arbitrary amplicon profiling (MAAP), microsatellite-primed PCR (MP-PCR), oligonucleotide ligation assay (OLA), randomly amplified hybridizing microsatellites (RAHM), randomly amplified microsatellite polymorphism (RAMPO), randomly amplified microsatellites polymorphism (RAMP), randomly amplified microsatellites (RAMS), random amplified polymorphic DNA (RAPD), retrotransposon-based insertion polymorphism (RBIP), retrotransposon-microsatellite amplified polymorphism (REMAP), restriction fragment length polymorphism RFLP), selective amplification of microsatellite polymorphic loci (SAMPLE), sequence characterized amplified regions (SCAR), single nucleotide polymorphism (SNP), single primer amplification polymorphism (SPAR), sequence related amplified polymorphism (SRAP), sequence-specific amplification polymorphism (S-SAP), single strand conformation polymorphism (SSCP), simple sequence length polymorphism (SSLP), sequence tagged microsatellite region (STAR), sequence-tagged microsatellite site (STMS), short tandem repeat (STR), sequence-tagged-site (STS), Target Region Amplification Polymorphism (TRAP), variable number of tandem repeats (VNTR), or a simple sequence repeat (SSR). In a related aspect, the DNA marker is cpSSR-2 or cpSSR-7. In one aspect of the technology, the DNA marker is cpSSR-2 or cpSSR-7. In another aspect of the technology, the DNA marker is a SNP in the intron of the gene sequence of rpoC1 that permits differentiation of the fertile and sterile cytoplasms of sunflower. In another aspect of the technology, the plant is alfalfa (*Medicago sativa*), onion (*Allium cepa*), maize (*Zea mays*), wheat (*Triticum aestivum*), rice (*Oryza sativa*), sunflower (*Helianthus annuus*), sorghum (*Sorghum bicolor*), carrot (*Daucus carota*), petunia (*Petunia hybrida*), canola (*Brassica napus*), sugarbeet (*Beta vulgaris*), or tobacco (*Nicotiana tabacum*). In other aspects of the technology, the predetermined threshold is either 1% or less or 0.1% or less.

DETAILED DESCRIPTION OF THE TECHNOLOGY

One of the practical problems associated with the implementation of this system in any crop species is that the cms line can often be contaminated with the normal male fertile line. In such cases, the rows of the cms line have plants from the normal male fertile line in various percentages. As both the cms and normal male fertile line are versions of the same line (nearly identical nuclear genotype) they are phenotypically identical and cannot be distinguished until flowering. By this time, it is too late to detect and rogue the plants of the normal male fertile line. In such case, during flowering, there are two different sources of pollen: from the restorer male parent line and from the contaminating normal male fertile line. Consequently, there are two possible types of crosses: (a) the legitimate or desired crosses of the type cms×restorer; and (b) the illegitimate or undesired crosses of the type cms×normal male fertile line. Since all seeds are harvested in bulk on the cms line, a variable percentage of seeds from the cross cms×normal male fertile line will contaminate the hybrid seed from the cross cms×restorer line. Since the illegitimate crosses give rise to non-hybrid cms seed, farmers using such undesirable types of seeds will obtain decreasing yields, in an amount which will depend on the degree of the original contamination.

Advance knowledge of the amount of contamination of the normal male fertile line in the cms line would advantageously allow for: (a) the ability to discard seed lots of the cms line with severe contamination of normal male fertile line; (b) detection and roguing of the contaminating plants of the normal male fertile line during the production of the hybrid seed or the multiplication of the cms line; and (c) the ability to conduct quality control of the hybrid seed.

Cytoplasmic male sterility has been described in more than 150 plant species (Kaul, 1988) and, in combination with the associated nuclear restorer of fertility genes, the cms system has been used extensively in plant breeding for the production of a range of F1 hybrid crops. In most cms mutants, anthers develop normally and microsporogenesis is arrested during or soon after meiosis (Kaul, 1988). Generally, the tapetum undergoes cellular degradation during meiosis of the meiocytes, followed soon after by the death of the immature microspores.

In cms plants, mitochondrial genomes have a set of genes identical to that of normal mitochondria (Satoh et al., 2004; Allen et al., 2007). Efforts to identify mitochondrial genes, has resulted in the discovery of aberrant open reading frames, consisting of fragments of mitochondrial genes and/or unknown sequences, usually with a chimeric structure. In fact, cms is associated with the expression of novel open reading frames (ORFs) in the mitochondrial genome in most species investigated to date (Schnable and Wise, 1998) or with the deletion of mitochondrial genes in tobacco (Gutierres et al., 1997). The novel ORFs are thought to have originated by aberrant recombination events in the plant mitochondrial genome. The DNA sequences of the novel ORFs often contain partial sequences of other mitochondrial genes and may be co-transcribed with functional mitochondrial genes (de la Canal, et al, 2001; Balk, et al., 2001).

To date, a number of aberrant ORFs, each producing unique polypeptides, have been reported to be associated with cms (Chase, 2007; Hanson and Bentolila, 2004). The aberrant ORFs have little in common, even when their phenotype is very similar. This suggests that the cms-associated aberrant ORFs have arisen independently during the course of angiosperm evolution (Kubo, 2007, 2008).

The present technology is based on the surprising discovery of a method to differentiate cms plants from their normal fertile counterparts by analyzing chloroplast genome.

The chloroplast genome in higher plants is highly conserved (Wolfe et al. 1987), which has had some practical implications for genetic research. Most importantly, the high degree of sequence conservation has enabled the use of heterologous hybridization probes and polymerase chain reaction (PCR) primers in unrelated species, thereby circumventing the need to clone chloroplast DNA (cpDNA) from each and every species (Olmstead and Palmer 1994). Universal PCR primer pairs have been constructed on the basis of conserved coding sequences of cpDNA genes and are used to amplify the DNA located between the primer binding sites (Taberlet et al. 1991; Demesure et al. 1995; Dumolin-Lapegue et al. 1997). A cpDNA marker system has been developed that is based on the occurrence of a certain type of "microsatellite" in the chloroplast genome (Powell et al. 1995). Microsatellites, also called "simple sequence repeats" or "SSR," are abundant polymorphic elements of eukaryotic nuclear genomes that consist of tandemly reiterated, short DNA sequence motifs (Wang et al. 1994; Field and Wills 1996). Size variation of SSRs is due to a variable repeat copy number and can be visualized by amplification, for example by PCR with pairs of flanking primers, followed by electrophoretic separation of the amplification products. Nuclear SSRs are often multi-allelic within and among populations, inherited in a co-dominant fashion, and fast and easy to type. Accordingly, SSRs have become the marker system of choice for genetic mapping, population genetics, and DNA profiling in plants (Powell et al. 1996; Weising et al. 1998).

A set of 10 consensus primer pairs based on multiple alignments of mononucleotide repeat-flanking regions in cpDNA from several mono- and dicotyledonous plant species has been described by (Powell and others 1995; Bryan and others 1999; Weising and Gardner 1999). Eight of the 10 primer pairs are ubiquitously applicable across dicotyledonous angiosperms, and reveal intra- and interspecific cpDNA polymorphisms within many genera of Angiosperms. (Weising & Gardner, 1999; Weissing et al, 2005; Borsch & Quandt, 2009). Since then, conserved primer pairs that flank cpSSRs have been identified from a number of angiosperm species.

EXAMPLES

Figures

FIG. 1 is a Table showing the sunflower genotypes used in this study.

FIG. 2 shows the products of amplification of a polymorphic marker targeting the cpSSR-7 of chloroplastic DNA from young leaves of different cms and normal fertile sunflower lines and commercial hybrids separated electrophoretically.

FIG. 3 shows the products of amplification of a polymorphic marker targeting the cpSSR-7 of chloroplastic DNA from seeds of different cms and normal fertile sunflower lines and commercial hybrids separated electrophoretically.

FIG. 4 shows the products of amplification of a polymorphic marker targeting the cpSSR-7 of chloroplastic DNA from a sunflower seed lot separated electrophoretically. This permits the detection of contaminating seeds from a normal fertile line into a seed lot of a sterile line.

FIG. 5 shows the products of amplification of a polymorphic marker targeting the cpSSR-2 of chloroplastic DNA from a maize seed lot separated electrophoretically. This permits the differentiation of sterile and fertile cytoplasms in maize.

FIG. 6 shows the products of amplification of a polymorphic marker targeting the cpSSR-2 of chloroplastic DNA from a wheat seed lot carrying the *Timopheevi* cytoplasm, separated electrophoretically. This permits the differentiation of sterile and fertile *Timopheevi* cytoplasms in wheat.

FIG. 7 shows the products of amplification of a polymorphic marker targeting the cpSSR-2 of chloroplastic DNA from a sorghum seed lot separated electrophoretically. This permits the differentiation of sterile and fertile cytoplasms in sorghum.

FIG. 8 shows partial nucleotide alignment of the complementary reverse sequences of the rpoC1 intron from sterile (SEQ ID NO:3) and fertile (SEQ ID NO:4) sunflower lines.

FIG. 9 shows partial nucleotide alignment of the complementary reverse sequences of the intron rpoC1 from sunflower lines RIG (SEQ ID NO:5), PET1 (SEQ ID NO:3), HA89 (SEQ ID. 4), PET2 (SEQ ID NO:6), ANN2 (SEQ ID NO:7), GIG1 (SEQ ID NO:8), ANN3 (SEQ ID NO:9), MAX1 (SEQ ID NO:10), PEF1 (SEQ ID NO:11), and ANN4 (SEQ ID NO:12) with different cytoplasms.

FIG. 10 shows the detection of SNP to differentiate fertile from sterile cytoplasms using Real Time PCR and SYBR Green I methodology. The plot displays the units of relative fluorescence (RFU) in function of numbers of amplification cycles of samples carrying the fertile and sterile cytoplasms. Using the same amount of cpDNA input in the PCR reactions, the early Ct value (Ct number of amplification cycles threshold) indicates the specific detection of samples with fertile cytoplasm.

FIG. 11 shows the detection of SNP to differentiate fertile seeds contaminating sterile seed lots. The plot displays the units of relative fluorescence (RFU) in function of the number of amplification cycles. Differences in Ct (number of amplification cycles threshold) values indicate different levels of contamination by seeds with fertile cytoplasm in the samples.

FIG. 12 shows a TaqMan assay for detection of fertile or "normal" cytoplasm. The sample carrying the fertile cytoplasm shows the lowest Ct value, indicating the specific identification of the polymorphism by the probe. Meanwhile, the sterile cytoplasm sample shows the highest Ct value, indicating that the polymorphism present in this samples was not detected.

FIG. 13 shows a TaqMan assay to determine fertile cytoplasm contamination levels. Ct values increase as a function of fertile cytoplasm contamination. The lower Ct value indicates the higher level of fertile cytoplasm contamination.

EXAMPLE 1

In this example, DNA polymorphisms in the chloroplast genome allowed for the identification of sterile and fertile versions of the same inbred line in sunflower. The species of sunflower employed is PET1-CMS, which was identified in an interspecies cross between *Helianthus petiolaris* and *Helianthus annuus* (Leclercq, 1969). PET1-CMS is associated with the expression of a novel mitochondrial gene, orf522, which encodes a 15-kD polypeptide (Horn et al., 1991; Laver et al., 1991; Monéger et al., 1994). The orf522 gene was created by a recombination event involving an inversion/insertion rearrangement to the atp1 gene (Köhler et al., 1991; Laver et al., 1991). The first 18 amino acids of ORF522 are identical to ORFB, which may be the plant homolog of yeast and mammalian ATPS, a subunit of the F 0F1-ATPase (Gray et al., 1998).

Several pairs of sterile PET1-CMS and fertile isolines of different genealogy were used, together with many restorer lines (CMSPET1 cytoplasm) and 6 commercial hybrids (PET1-CMS cytoplasm). The table depicted in FIG. 1 shows the different species of plant lines employed in this example, showing genotype, sterile/fertile status, and type of line or hybrid.

Genomic DNA was isolated from young leaves of different CMS and fertile sunflower lines and commercial hybrids using modifications of the cetyl trimethylammonium (CTAB) procedure (Weising et al. 1995). DNA concentrations were determined electrophoretically against known amounts of DNA as standards. For PCR, DNA samples were adjusted to a concentration of 20 ng/µl.

The cpSSR-7 marker was amplified by PCR from chloroplastic DNA (cpDNA). The PCR reaction was carried out in a 15 µl final volume containing 25 ng cpDNA, 0.5 U Taq Platinum DNA Polymerase (Invitrogen Carlsbad, Calif.) in 1×PCR Buffer (Invitrogen), 0.2 mM each dATP, dCTP, dGTP and dTTP, and 0.45 µM each forward and reverse primers (cpSSR-7F: CAACATATACCACTGTCAAG (SEQ ID NO:17) and cpSSR-7R: ACATCATTATTG-TATACTCTTTC (SEQ ID NO:18)), under the following conditions: 95° C. for 3 minutes; followed by 10 cycles at 94° C. for 30 seconds, 58° C. for 30 seconds (−1° C./cycle), 72° C. for 45 seconds. The touchdown cycles were followed by 30 cycles of 94° C. for 30 seconds, 48° C. for 30 seconds, and 72° C. for 45 seconds, with a final extension of 72° C. for 2 minutes. Reactions were conducted using a PTC-200 (MJ Research, Waltham, Mass.) thermal cycler.

All the genetic materials (lines or hybrids) which present the PET1-CMS cytoplasm conferring male sterility in sunflower could be differentiated from those presenting the fertile or "normal" cytoplasm by means of many markers targeting SSRs in the chloroplasts genome. As an example, amplification of the DNA marker cpSSR-7 with the pair of primers cpSSR-7F and cpSSR-7R resulted in a PCR product of 125 bp in those genotypes with PET1-CMS cytoplasm (sterile cytoplasm), while a PCR product of 122 bp was produced from the genetic materials with normal or fertile cytoplasm. These results are depicted in FIG. 2, which shows the products of amplification of a polymorphic marker targeting the cpSSR-7, separated electrophoretically.

All of the materials within the PET1-CMS cytoplasm may be distinguished from the materials bearing a normal or fertile cytoplasm by the size of the fragment amplified by the polymorphic marker cpSSR-7. This indicates that the polymorphism in the mitochondrial genome conferring the sterility/fertility in sunflower may be assessed by means of a polymorphism in the chloroplast genome.

EXAMPLE 2

In this example, DNA polymorphisms useful for distinguishing sterile and fertile versions of the same line, were detected using DNA from proplastids occurring in the seed. The method described in the previous Example only has relevance and utility as a technological tool if the DNA can be extracted from the seeds of a given species. Otherwise, the method would require significant investments in space (generally greenhouse or climatic chamber space), light, time, and work, in order to sow the seeds and expect the adequate time to sample leaf tissue in order to extract cpDNA from them.

In the seeds of crop plants, plastids are in an undifferentiated form known as proplastids (Wise, 2006). Upon extraction of DNA from proplastids, PCR amplification was carried out as described previously. A polymorphic band which easily distinguished the sterile and fertile lines was obtained using the cpDNA extracted from seeds, exactly the same as that obtained from cpDNA extracted from leaves. This is depicted in FIG. 3, which shows the products of amplification of a polymorphic marker targeting the cpSSR-7 of cpDNA from proplastids from the seed separated electrophoretically. This confirms that the method used to distinguish both fertile and sterile cytoplasms and based on polymorphisms of the chloroplast genome can be assessed not only from leaves, as described in Example 1, but also from dried seeds.

EXAMPLE 3

In this example, DNA polymorphisms in the chloroplast genome permit the detection of contaminating seeds from a normal fertile line into a seed lot of a sterile line. In this example, the PCR reaction was carried out in a 15 µl final volume containing 25 ng cpDNA, 0.5 U Taq Platinum DNA Polymerase (Invitrogen Carlsbad, Calif.) in 1×PCR Buffer (Invitrogen), 0.45 mM each dATP, dGTP, and dTTP, 0.40 mM dCTP and 0.75 mM Cy5.5-dCTP, and 0.45 µM each forward and reverse primers. The PCR program was employed was the same as described in previous Examples.

After the PCR amplification the sample were cleaned up using NucleoFast 96 PCR (Macherey-Nagel). Samples (0.25 µl) were loaded on 6.5% polyacrylamide gel in 1×TBE and electrophoresed at 1500 V, 40 mA, 30 W, at 45° C. on a LiCor 4300 DNA Analyzer (Li-Cor Biosciences, Lincoln, Nebr.). Images were visually analyzed using Adobe Photoshop (Adobe Systems, Inc, San Jose, Calif.).

These results are depicted in FIG. 4, which shows the products of amplification of a polymorphic marker targeting the cpSSR-7 of genomic DNA from proplastids from the seed of a lot of sunflower seeds separated electrophoretically. This permits the detection of contaminating seeds from a normal fertile line into a seed lot of a sterile line.

EXAMPLE 4

In this example, DNA polymorphisms in the chloroplast genome permit differentiation of sterile and fertile cytoplasms in a different plant species, maize. In maize, several sterile cytoplasms have been developed. A-cytoplasm is a sterile cytoplasm widely used in hybrid seed production. Using the method described in the previous Examples, FIG. 5 shows that the polymorphism of the cpSSR-2 marker (amplified with the primers cpSSR-2F: GATCCCGGACG-TAATCCTG (SEQ ID NO:19) and cpSSR-2R: ATCGTAC-CGAGGGTTCGAAT (SEQ ID NO:20)) is able to differentiate sterile lines carrying the A cytoplasm from their fertile counterparts (isolines) bearing a normal or fertile cytoplasm.

EXAMPLE 5

In this example, DNA polymorphisms in the chloroplast genome permit differentiation of sterile and fertile cytoplasms of wheat. In wheat, one of the most commonly used cytoplasms for hybrid seed production is the "Timopheevi-cytoplasm." Using the method described in the previous Examples, FIG. 6 shows that it is possible to differentiate sterile lines carrying the Timopheevi cytoplasm from their fertile counterparts bearing a normal or fertile cytoplasm by using the polymorphism of the cpSSR-2 marker.

EXAMPLE 6

Using the method described in the previous Examples, FIG. 7 shows that DNA polymorphisms in the chloroplast genome permit differentiation of sterile and fertile cytoplasms in sorghum.

While the present technology has been disclosed with reference to certain aspects and embodiments, persons of ordinary skill in the art will appreciate that numerous modifications, alterations, and changes to the described aspects are possible without departing from the sphere and scope of the present technology. Accordingly, it is intended that the present technology not be limited to the described aspects and embodiments described herein, but that the technology be understood consistent with the full spirit and scope in which they are intended to be understood, including equivalents of the particular aspects and embodiments described herein.

EXAMPLE 7

Previous examples make use of polymorphisms in the length of fragments from chloroplastic SSRs. In this example, using non-coding sequence primers, the intron sequence of the rpoC1 gene was amplified by PCR from proplastid DNA extractions in order to differentiate fertile and sterile sunflower lines.

The PCR reaction was carried out in a 25 µl final volume containing 50 ng cpDNA, 0.5 U Taq Platinum DNA Polymerase (Invitrogen Carlsbad, Calif.) in 1×PCR Buffer (Invitrogen), 0.1 mM dNTPs, 2.5 mM MgCl$_2$, 0.3 µM of each primer (SEQ ID NO:1: GAATTAGGGATGTAT-TCAAGACGC and SEQ ID NO:2: GGAGT-TCTCGCTTTCAGATTCTAG), and 4% DMSO under the follow conditions: 94° C. for 5 minutes; 35 cycles at 94° C. for 1 minute, 55° C. for 20 seconds, and 72° C. for 30 seconds. Reactions were conducted using a PTC-200 (MJ Research, Waltham, Mass.) thermal cycler. The PCR products were sequenced.

Surprisingly, all the genetic materials (lines or hybrids) which present the PET1-CMS cytoplasm conferring male sterility in sunflower have a sequence set forth as SEQ ID NO:3 that is different from the sequence of the genetic materials presenting the fertile or "normal" cytoplasm (SEQ ID NO:4) by a SNP detected in the intron of the rpoC1 gene sequence and coded as "G506T" (FIG. 8). At the SNP position, lines carrying PET1-CMS cytoplasm show a T and the fertile or "normal" sunflower cytoplasm lines display a G in the intron rpoC1 sequence. That is, the polymorphism at position 506 of the rpoC1 intron represents a polymorphism, which allows for the discrimination between fertile and sterile lines.

EXAMPLE 8

In this example, intron sequences of the chloroplastic gene rpoC1 from several different cytoplasms conferring male-sterility in sunflower and coded as RIG, PET2, ANN2, GIG1, ANN3, MAX1, PEF1, ANN4 were amplified, sequenced, aligned and compared to detect SNPs.

The obtained sequences are set forth as SEQ ID NOs:5-12 and are aligned and compared in FIG. 9. This figure shows the partial nucleotide alignment of the complementary reverse sequences for the rpoC1 intron of the above-mentioned sterile cytoplasms (SEQ ID NO:3) and the fertile or "normal" cytoplasm (SEQ ID NO:4). Surprisingly, all the tested cytoplasms which traced back to different wild Helianthus species, with the exception of PET2 (SEQ ID NO:6), show exactly the same polymorphism with respect to the fertile or "normal" cytoplasm as described in Example 7. Thus, the unexpected results show that the SNP G506T can be used to differentiate, detect or identify at the molecular level the sterile cytoplasms PET1, RIG, ANN2, GIG1, ANN3, MAX1, PEF1, and ANN4 from the normal or fertile cytoplasm. The PET2 cytoplasm, on the other hand, can also be differentiated from the fertile cytoplasm by another SNP at the same position (506). In fact, at this position PET2 shows an A meanwhile the fertile or "normal" cytoplasm displays a G as was shown in Example 7. This later SNP, useful to identify PET2 sterile cytoplasm from the fertile cytoplasm, was coded as G506A.

EXAMPLE 9

In this Example, detection of SNP present in the intron rpoC1 of fertile or "normal" cytoplasm was performed with proplastid DNA as input by a Real Time PCR method using allele-specific primers and the green fluorescent dye SYBR Green I (Invitrogen).

Real Time PCR reactions were performed with the iQCycler thermocycler iQ4 (Bio-Rad). The PCR reaction was carried out in a 25 µl final volume containing 50 ng cpDNA, 0.5 U Taq Platinum DNA Polymerase (Invitrogen Carlsbad, Calif.) in 1×PCR Buffer (Invitrogen), 0.1 mM dNTPs, 2.5 mM MgCl$_2$, 0.15 µM of each primer ("G506-R", SEQ ID NO.13: ACGAGGTATAACTATAAATTCTTATGAAA<u>G</u> and "rpoC1-Forward", SEQ ID NO. 1: GAATTAGGGAT-GTATTCAAGACGC), 0.5×SYBR Green I and 4% DMSO. The PCR conditions were as follows: 94° C. for 5 minutes; 35 cycles at 94° C. for 30 minutes, 58.5° C. for 20 seconds, and 72° C. for 30 seconds. All PCR reactions were performed in triplicate for each sample.

Real Time PCR methodology based on allele-specific primers was able to identify the G at the position 506 which unambiguously differentiate the fertile cytoplasm from all the other sterile cytoplasms tested (FIG. 10).

EXAMPLE 10

In this Example, DNA polymorphisms in the chloroplastic genome permit the detection of contaminating seeds from a normal fertile line into a seed lot of a sterile line. The PCR reactions were performed using the Real Time PCR strategy detailed in Example 9. The cpDNA from four different samples carrying four different contamination levels (10, 5, 2 and 0.2% of seeds of a fertile cytoplasm line into a bulk of seeds of a sterile line) were obtained. The cpDNAs were normalized to use the same amount in the PCR reactions. All PCR reactions were performed in triplicate for each sample.

Thus, the Real Time PCR methodology based on SYBR Green I is reliably sensitive enough to detect as less as 1 fertile or "normal" seed into a pool of 499 seeds with sterile cytoplasm (i.e., 0.2% of contamination), as shown in FIG. 11.

EXAMPLE 11

In this Example, detection of SNP present in the intron rpoC1 of fertile or "normal" cytoplasm was performed using a TaqMan assay (PE Applied Biosystems, Foster City, Calif.) based on an allele-specific oligonucleotide probe. The sequences of the primers and probe are as follows: "PTQF-1", SEQ ID NO:14, CTA-CAAAAGAAAAAGTCTTTTTTTACGAGGTATAACT and "PTQR-1" SEQ ID NO:15: TGTATTCAAGACGCTC-CCCAAAA, and "PBTQ1", SEQ ID NO:16: (FAM)-ATC-TATGGTCGCTTTCAT-(MGB). Real Time PCR reactions were performed with the iQCycler thermocycler iQ4 (Bio-Rad). The PCR reaction was carried out in 25 µl final volume using 2× TaqMan SNP Genotyping (PE Applied Biosystems), 20×SNP genotyping assay, 10 µl DNA at 10 ng/µl using the next conditions: 95° C. 10 minutes, 40 cycles 92° C. 15 seconds 60° C. 1 minute. All PCR reactions were performed in triplicate for each sample.

FIG. 12 shows the specific detection performed by FAM-labeled probe of the fertile cytoplasm differentiating fertile lines carrying the fertile cytoplasm from their sterile counterparts.

EXAMPLE 12

In this Example, DNA polymorphisms in the chloroplastic genome permit the detection of contaminating seeds from a normal fertile line into a seed lot of a sterile line. The PCR reactions were performed using the Real Time PCR strategy detailed in previous examples. The cpDNA was obtained from four different samples artificially contaminated to generate four different contamination levels (5, 1, 0.5, and 0.1% of seeds with fertile cytoplasm into a bulk of seeds with sterile cytoplasm). The cpDNAs were normalized to use the same amount in the PCR reactions. All PCR reactions were performed in triplicate for each sample.

The impressive results obtained indicate that Real Time PCR methodology based on TaqMan assay is reliably sensitive enough to detect as low as 1 fertile or "normal" seed into a pool of 999 sterile seeds (i.e., 0.1%), as shown in FIG. 13, allowing an early detection of contamination traces in sterile seed lots.

What is claimed is:

1. A method for differentiating normal fertile and sterile counterparts of an inbred line of a sunflower (*Helianthus annuus*) plant crop having a cytoplasmic or nuclear-cytoplasmic system of male sterility comprising the steps of:
   (a) extracting chloroplastic DNA comprising one or more DNA markers selected from the group consisting of the G506T SNP in the intron of the gene rpoC1 and the G506A SNP in the intron of the gene rpoC1 from the seeds of the sunflower plant crop;
   (b) amplifying the chloroplastic DNA comprising one or more DNA markers selected from the group consisting of the G506T SNP in the intron of the gene rpoC1 and the G506A SNP in the intron of the gene rpoC1 to produce amplified fragments of the one or more DNA markers; and,
   (c) assaying the amplified fragments of the one or more DNA markers to differentiate normal fertile and sterile counterparts of an inbred line of the sunflower plant crop having a cytoplasmic or nuclear-cytoplasmic system of male sterility.

2. The method of claim 1, wherein the chloroplastic DNA is extracted from seeds of the plant crop.

3. The method of claim 1, wherein the DNA marker is amplified and detected using Real Time PCR methodology.

4. The method of claim 3, wherein the DNA marker is amplified using primers set forth in SEQ ID NOs: 1 and 13.

5. The method of claim 1, wherein the DNA marker is amplified and detected using a TAQMAN assay.

6. The methodology of claim 5, wherein the DNA marker is amplified using the primers set forth in SEQ ID NOs:14 and 15 and the amplicon is probed with a fluorophore-labeled probe with a sequence set forth in SEQ ID NO:16.

7. A method for detecting plant seed contamination of normal fertile plant seeds among cytoplasmic male sterile plant seeds, of an inbred line of a sunflower (*Helianthus annuus*) plant crop having a cytoplasmic or nuclear-cytoplasmic system of male sterility, comprising the steps of:
   (a) extracting chloroplastic DNA comprising one or more DNA markers selected from the group consisting of the 0506T SNP in the intron of the gene rpoC1 and the 0506A SNP in the intron of the gene rpoC1 from the seeds of the sunflower plant crop;
   (b) amplifying the chloroplastic DNA comprising one or more DNA markers selected from the group consisting of the 0506T SNP in the intron of the gene rpoC1 and the 0506A SNP in the intron of the gene rpoC1 to produce amplified fragments of the one or more DNA markers; and
   (c) assaying the amplified fragments of the one or more DNA markers to detect plant seed contamination of normal fertile plant seeds among cytoplasmic male sterile plant seeds of an inbred line of sunflower plant crop having a cytoplasmic or nuclear-cytoplasmic system of male sterility;
   wherein a seed lot is selected based on a level of contamination of normal fertile plant line seeds being below a predetermined threshold, wherein the predetermined threshold is 1% or less of seeds with fertile cytoplasm into a bulk of seeds with sterile cytoplasm; and
   (d) selecting the seed lot if the level of contamination of normal fertile plant line seeds is below the predetermined threshold.

8. The method of claim 7, wherein the DNA marker is amplified and detected using Real Time PCR methodology.

9. The method of claim 8, wherein the DNA marker is amplified using primers set forth in SEQ ID NOs: 1 and 13.

10. The method of claim 7, wherein the DNA marker is amplified and detected using a TAQMAN assay.

11. The methodology of claim 8, wherein the DNA marker is amplified using the primers set forth in SEQ ID NOs:14 and 15 and the amplicon is probed with a fluorophore-labeled probe with a sequence set forth in SEQ ID NO:16.

12. The method of claim 7, wherein the predetermined threshold is 0.1% or less.

13. A method for differentiating normal fertile and sterile counterparts of an inbred line of a plant crop having a cytoplasmic or nuclear-cytoplasmic system of male sterility comprising the steps of:
   (a) extracting chloroplastic DNA comprising one or more DNA markers selected from the group consisting of cpSSR-2 and cpSSR-7;
   (b) amplifying the chloroplastic DNA comprising one or more DNA markers selected from the group consisting of cpSSR-2 and cpSSR-7 to produce amplified fragments of the one or more DNA markers; and,
   (c) assaying the amplified fragments of the one or more DNA markers to differentiate between normal fertile and sterile counterparts of the inbred line of the plant crop having a cytoplasmic or nuclear-cytoplasmic system of male sterility.

14. The method of claim 13, wherein the chloroplastic DNA comprising one or more DNA markers selected from the group consisting of cpSSR-2 and cpSSR-7 is amplified using PCR.

15. The method of claim 14, wherein the chloroplastic DNA comprising one or more DNA markers selected from the group consisting of cpSSR-2 and cpSSR-7 is amplified using a cpSSR-2 forward primer comprising the sequence set forth in SEQ ID NO:17 and a cpSSR-2 reverse primer comprising the sequence set forth in SEQ ID NO:18.

16. The method of claim 14, wherein the chloroplastic DNA comprising one or more DNA markers selected from the group consisting of cpSSR-2 and cpSSR-7 is amplified using a cpSSR-7 forward primer comprising the sequence set forth in SEQ ID NO:19 and a cpSSR-7 reverse primer comprising the sequence set forth in SEQ ID NO:20.

17. The method of claim 13, wherein the chloroplastic DNA is extracted from seeds of the plant crop.

18. The method of claim 13, wherein the plant is alfalfa (*Medicago sativa*), onion (*Allium cepa*), maize (*Zea mays*), wheat (*Triticum aestivum*), rice (*Oryza sativa*), sunflower (*Helianthus annuus*), sorghum (*Sorghum bicolor*), carrot (*Daucus carota*), petunia (*Petunia hybrida*), canola (*Brassica napus*), sugarbeet (*Beta vulgaris*), or tobacco (*Nicotiana tabacum*).

19. A method for detecting plant seed contamination of normal fertile plant seeds among cytoplasmic male sterile plant seeds, of an inbred line of plant crop having a cytoplasmic or nuclear-cytoplasmic system of male sterility, comprising the steps of:
   (a) extracting chloroplastic DNA comprising one or more DNA markers selected from the group consisting of cpSSR-2 and cpSSR-7;
   (b) amplifying the chloroplastic DNA comprising one or more DNA markers selected from the group consisting of cpSSR-2 and cpSSR-7 to produce amplified fragments of the one or more DNA markers; and
   (c) assaying the amplified fragments of the one or more DNA markers to detect plant seed contamination of normal fertile plant seeds among cytoplasmic male sterile plant seeds of an inbred line of plant crop having a cytoplasmic or nuclear-cytoplasmic system of male sterility;
   wherein a seed lot is selected based on a level of contamination of normal fertile plant line seeds being below a predetermined threshold, wherein the predetermined threshold is 1% or less of seeds with fertile cytoplasm into a bulk of seeds with sterile cytoplasm; and
   (d) selecting the seed lot if the level of contamination of normal fertile plant line seeds is below the predetermined threshold.

20. The method of claim 19, wherein the chloroplastic DNA comprising one or more DNA markers selected from the group consisting of cpSSR-2 and cpSSR-7 is amplified using PCR.

21. The method of claim 20, wherein the chloroplastic DNA comprising one or more DNA markers selected from the group consisting of cpSSR-2 and cpSSR-7 is amplified using a cpSSR-2 forward primer comprising the sequence set forth in SEQ ID NO:17 and a cpSSR-2 reverse primer comprising the sequence set forth in SEQ ID NO:18.

22. The method of claim 20, wherein the chloroplastic DNA comprising one or more DNA markers selected from the group consisting of cpSSR-2 and cpSSR-7 is amplified using a cpSSR-7 forward primer comprising the sequence set forth in SEQ ID NO:19 and a cpSSR-7 reverse primer comprising the sequence set forth in SEQ ID NO:20.

23. The method of claim 19, wherein the predetermined threshold is 0.1% or less.

24. The method of claim 19, wherein the plant is alfalfa (*Medicago sativa*), onion (*Allium cepa*), maize (*Zea mays*), wheat (*Triticum aestivum*), rice (*Oryza sativa*), sunflower (*Helianthus annuus*), sorghum (*Sorghum bicolor*), carrot (*Daucus carota*), petunia (*Petunia hybrida*), canola (*Brassica napus*), sugarbeet (*Beta vulgaris*), or tobacco (*Nicotiana tabacum*).

\* \* \* \* \*